US00PP19436P3

(12) United States Plant Patent
Gradziel et al.

(10) Patent No.: US PP19,436 P3
(45) Date of Patent: Nov. 11, 2008

(54) ALMOND VARIETY NAMED 'SWEETHEART'

(50) Latin Name: *Prunus dulcis*
Varietal Denomination: Sweetheart

(75) Inventors: Thomas Gradziel, Davis, CA (US); Mary Ann Thorpe, Davis, CA (US); Dale Kester, deceased, late of Davis, CA (US); by Nancy K. Baysinger, legal representative, California, MD (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/707,431

(22) Filed: Feb. 15, 2007

(65) Prior Publication Data

US 2008/0201808 P1 Aug. 21, 2008

(51) Int. Cl.
*A01H 5/00* (2006.01)

(52) U.S. Cl. ..... Plt./155

(58) Field of Classification Search ..... Plt./155
See application file for complete search history.

*Primary Examiner*—Annette H Para
(74) *Attorney, Agent, or Firm*—Morrison & Foerster LLP

(57) ABSTRACT

An improved *Prunus dulcis* variety is provided that is well suited for serving as a replacement for the premium quality 'Marcona' variety (non-patented in the United States). A distinctive heart-shape kernel in combination with very high kernel lipid quality is displayed. Good bloom overlap is displayed with the widely-grown 'Nonpareil' variety (non-patented in the United States) and pollen is cross-compatible with 'Nonpareil' and all major California almond varieties. The tree exhibits an upright-spreading growth habit with good productivity. Desirable fruit and kernel characteristics for shelled and processed almond production are displayed.

3 Drawing Sheets

Botanical/commercial classification: (*Prunus dulcis*)/new almond variety.
Variety denomination: 'Sweetheart'.

BACKGROUND OF THE INVENTION

A major objective of almond breeding programs is the development of new varieties with high kernel quality capable of acting as a pollinizer variety for the California almond variety 'Nonpareil' (non-patented in the United States). With recent findings that high proportions of the monounsaturated kernel oil, particularly oleic acid, confer significant health benefits to consumers, this trait has been included as a component of kernel quality.

Pollinizer varieties are required for 'Nonpareil' as well as all other commercial California almond varieties since they are self-sterile, thus requiring pollen from cross-compatible varieties for successful seed set. Because of its high market quality, 'Nonpareil' has become the leading California almond variety with approximately 45% of the total California acreage in 2005. Nonpareil's high market value results, in part, from its exceptional uniformity in kernel shape and composition. Nonpareil's relatively low kernel oleic acid proportion of 67.5% results in a lower phytonutrient value, greater susceptibility to kernel rancidity in storage, and poorer quality when roasted.

To provide the market with a premium quality roasting almond, California growers began planting the very high kernel-quality Spanish variety 'Marcona' in the mid-1990's. While consistently achieving retail market prices of approximately 4 times the 'Nonpareil' price, the 'Marcona' variety appears poorly suited for California growing conditions owing to its undesirable growth habit, greater disease susceptibility, and its very thick and hard shell which is incompatible with most California shelling equipment and results in kernel-to-nut (kernel plus shell) ratios of less than 35%.

The 'Sweetheart' almond is primarily an almond that would be grown and sold as a commercial nut rather than as an ornamental or 'backyard' tree. The most comparable example of this type of almond is the Spanish 'Marcona' almond variety. In California, 'Marcona' is grown only for commercial production of a premium quality, high market priced roasting almond. The 'Sweetheart' variety is targeted at the same market, as well as an effective pollinizer for 'Nonpareil'. Currently no other almond variety combines similar characteristics with good adaptation to the California environment and production practices.

Because it is a recently introduced variety with a limited marketing niche, current plantings of the 'Marcona' variety in California are estimated at under 2000 acres. Plantings of the 'Marcona' variety in Spain are estimated to exceed 50,000 acres. It could reasonably be expected that acreage of 'Sweetheart' would readily increase as its greater compatibility to the California environment and processing practices are recognized. Expectation of 5000 or more acres of this new cultivar eventually being planted is probably not unrealistic.

SUMMARY OF THE INVENTION

The new 'Sweetheart' variety is the product of recent breeding efforts to introgress novel genes from closely related germplasm in order to overcome genetic constraints within current cultivated almond germplasm. An initial objective was the transfer of pollen-pistil self-compatibility from peach to develop a self-fruitful almond. The 'Sweetheart' variety has demonstrated moderate levels of self-compatibility which have contributed to greater crop-set uniformity in years where poor weather has limited the traditional insect-mediated cross-pollination, but self-compatibility levels have not been consistently high enough to be considered a "stand-alone" self-fertile variety. With an average kernel oleic acid content of 74.9%, the 'Sweetheart' variety has the highest oleic acid proportion of any California variety or breeding selection tested, conferring a high phytonutrient value to consumers, greater resistance to kernel rancidification in storage, and a highly desirable 'Marcona'-like flavor when roasted. The cordate or heart-shape of the kernel is very similar to the 'Marcona' kernel and has particular marketing value since California almonds are currently advertised as the 'heart-healthy' nut to emphasis the demonstrated phytonutrient value of almond consumption in reducing heart disease. In addition, the 'Sweetheart' variety has a well sealed but thin, paper shell resulting in full compatibility with California processing equipment and a high kernel-to-nut ratio of approximately 55%.

The 'Sweetheart' variety also displays a very low proportion of double-kernels (less than 1%) and improved resistance to worm damage (primarily navel orangeworm and Indian meal moth) during post-harvest storage. The 'Sweetheart' variety is fully cross-compatible with 'Nonpareil' and all commercial California almond varieties, and consistently flowers 2 to 4 days after 'Nonpareil' variety making it an effective pollinizer for the later 'Nonpareil' bloom. Test plantings have been evaluated in both the Sacramento Valley and San Joaquin Valley almond production areas. Kernel yields have been comparable to 'Nonpareil' in 14 and 16-year old test plantings. Harvest is just after 'Nonpareil' but before other major varieties making it well adapted to current orchard production practices.

The 'Sweetheart' variety of almond demonstrates a medium-sized heart-shaped kernel with a very high oil quality, making it comparable to the unpatented premium Spanish variety 'Marcona'. Unlike 'Marcona', the 'Sweetheart' variety has a high kernel-to-nut crack-out ratio, improved kernel pest resistance and is well adapted to California Central Valley growing conditions. The 'Sweetheart' variety is cross-compatibility with 'Nonpareil' and has good bloom overlap with 'Nonpareil' bloom and so is an effective pollenizers of 'Nonpareil'. Harvest of 'Sweetheart' is 1–2 weeks after 'Nonpareil' and so does not interfere with this and other major varieties. The 'Sweetheart' tree is upright-spreading and vigorous. Fruit production occurs on a combination of terminal and lateral shoots and spurs.

Since the early 1950s, many thousands of seedlings of *Prunus dulcis* have been developed and evaluated and the new variety 'Sweetheart', which was evaluated under the individual seedling designation number 'SB13,36-52', is the product of this breeding effort. The original almond seedling population from which this variety was selected was produced by routine crosses made in 1964 as part as the Calif. Expt. Stat. Proj. 739-Almond Breeding Project carried out in the Dept. of Pomology, University of California, Davis. Nursery trees of the seedling population from this cross were initially planted in Seedling Block (SB) 13 near Winters, Calif. in the spring of 1965. The population was identified as 6422 (the 22$^{nd}$ cross made in 1964) with the following pedigree: unpatented seed parent: SB3, 54-39E [Sel5-15{'Lukens Honey' peach×'Mission' almond}×'Nonpareil' almond]×(as pollen parent) unpatented almond breeding line Sel 25-26. The first observations of the 62 resultant seedling trees of this population were recorded in 1967 and resulted in 2 selections, which were further reduced to 1 in 1972. Selection 'SB 13, 36-52" refers to the field block, row and tree location of the original seedling (Seedling Block 13, row 36, tree 52).

Two clonal trees of SB13, 36-52 (F7,5-9 and F7,5-10) were propagated by T-budding near Winters, Calif. in 1972 but in 1976 this selection was judged as unacceptable for commercial release because only moderate levels of self-compatibility were displayed and the heart-shaped kernel was deemed incompatible with California markets.

Seed were harvested from F7, 5-10. In 1991, a high kernel oil quality for roasting was identified resulting in SB13,36-52 being placed in a 1994 test planting in Arbuckle, Calif.

Clean, virus tested stock of SB13,36-52 was designated by the Accession Number 3-53-1-93 (3 codes for almond, 53 is the unique clone number, 1 to source, and 93 indicates to the year planted).

Based on its promising performance, particularly its close resemblance to the very high kernel quality unpatented Spanish variety 'Marcona', its cross-compatibility with Nonpareil, and its good tree and nut qualities, selection 'SB13,36-52' was selected by as a candidate for release.

BRIEF DESCRIPTION OF THE PHOTOGRAPHS

BOTANICAL DESCRIPTION OF THE PLANT

Figure 1:
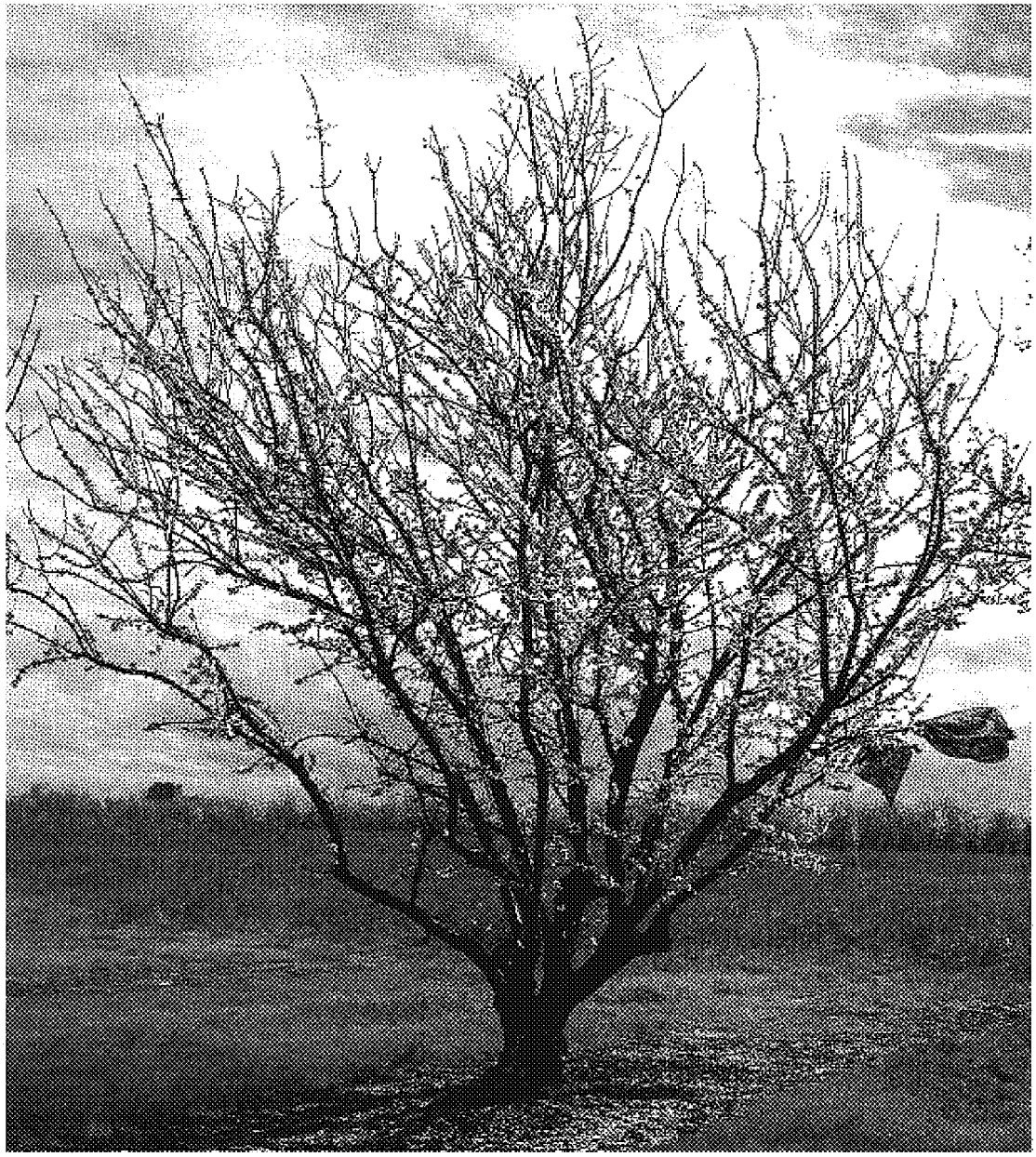
FIG. 1 shows the 'Sweetheart' tree. The approximate age of the 'Sweetheart' tree shown in FIG. 1 is 16 years.
Figure 2:
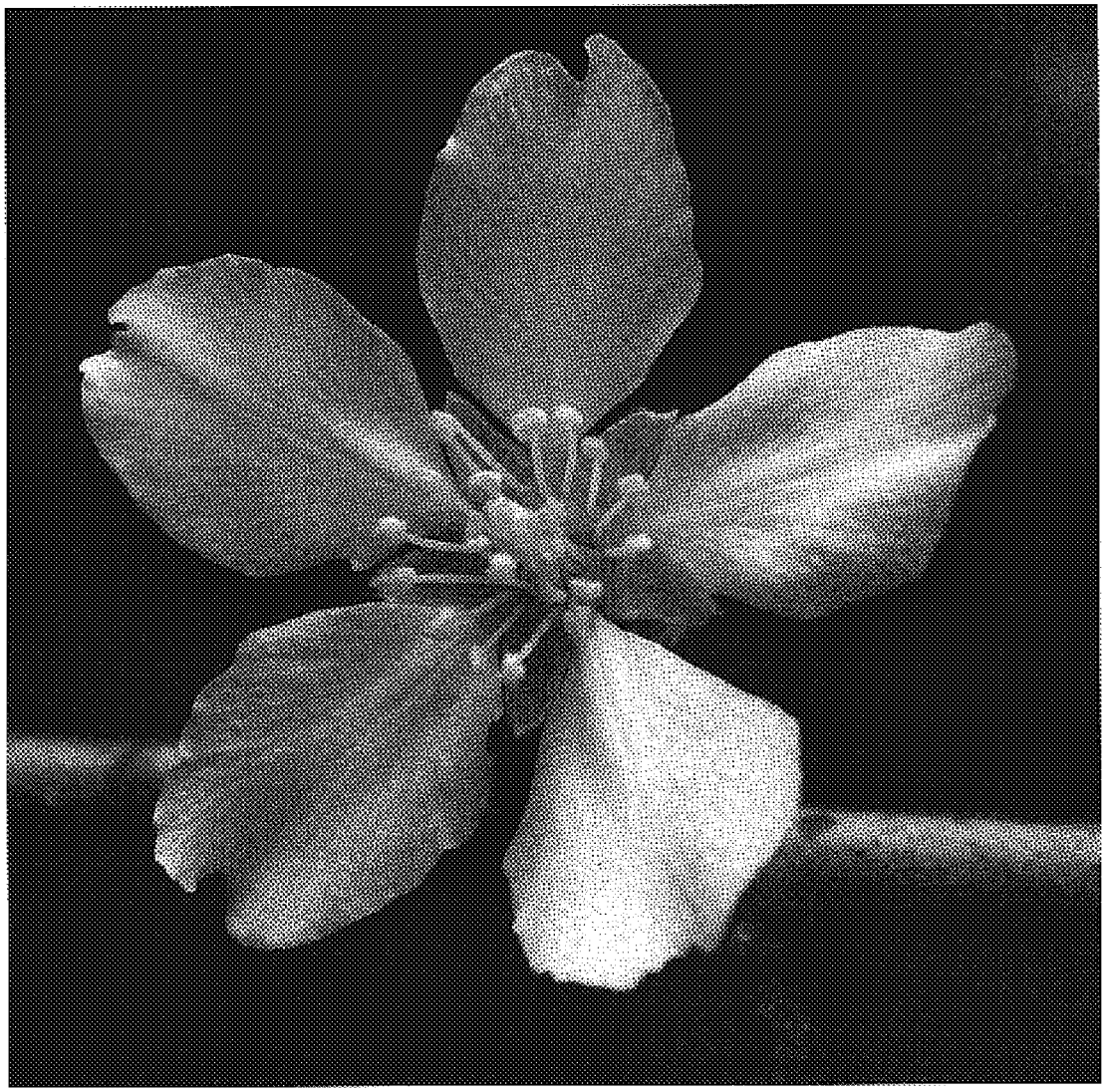
FIG. 2 shows the flower of the 'Sweetheart' tree.
Figure 3:
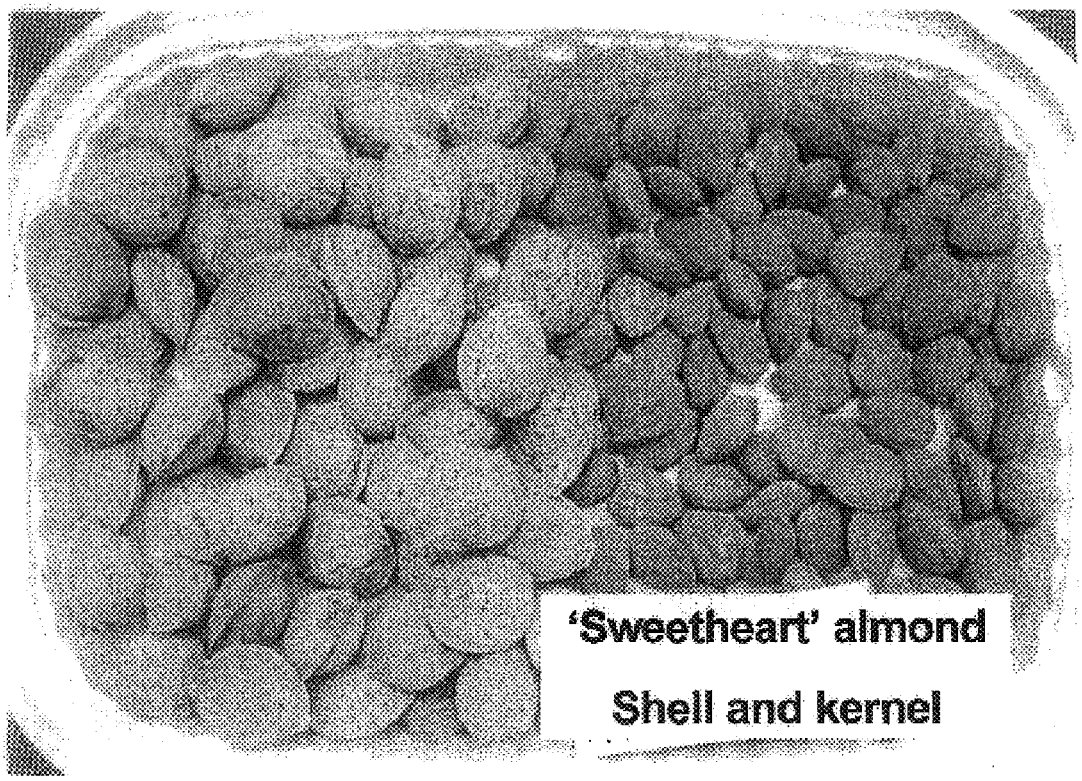
FIG. 3 shows the kernel and shell (endocarp or stone) of 'Sweetheart'.

The following is a detailed horticultural description of the new cultivar obtained from vegetatively propagated progeny observed during the 2004, 2005 and 2006 growing seasons. The approximate age of the trees described herein is 14 years. The rootstock is identified as Nemaguard rootstock. The tree can be grown in its own roots. The trees were grown at the Wolfskill Experimental Orchards of the University of California located at Winters, Calif., the Nickels Soils laboratory at Arbuckle, Calif., and at the Foundation Plant Service plots at Davis, Calif. Color designations are presented with reference to the "Dictionary of Color" by Maerz and Paul, First Edition (1930).

Tree: The tree size is medium. When compared with the 'Nonpareil' variety, the present almond tree is similar, but has a more spreading growth habit. Typical height and typical width of a 10-year old 'Sweetheart' tree is: Height of 22 feet (6.7 meters) and width of 20 feet (6.1 m).

The tree shape is upright-spreading. The density is moderate, allowing good light penetration to interior wood.

The vigor is moderate, usually 6 to 18 in. (10 to 45 cm) of current season terminal shoot growth typical for mature, bearing tree.

The regularity of bearing, generally, is regular, and occurs predominantly from spurs which are two years old or older.

Trunk: The form of the trunk is generally medium as compared with other common almond cultivars.

The surface texture of the trunk bark for a 10-year-old tree is rough with dark-gray (56-A-1) narrow forking fissures with smoother, silver-gray (11-B-1) ridges having 1–2 cm lenticel scars. Typical trunk diameter for 10-year-old tree at 12 in. (0.3 m) above ground height above the ground is 32 in (0.81 m).

Branches: The form of the branches are upright spreading, having a regular, slightly curved pattern of branching. The surface texture of the branch bark is smooth to glossy with horizontal lenticels.

The branch color is red-brown (8-L-6) becoming increasingly gray-brown with age.

The form of the branches have current year laterals typically originating at the mid-section of longer shoots with fairly uniform branching angles of 45 to 60 degrees. New growth is approximately 10 centimeters to about 45 centimeters (about 6 to about 18 inches) at the tops of mature, bearing trees.

Typical branch diameter for a branch of a specified age is 5–8 mm diameter at the terminal end of 1-year-old branches. The node number is approximately 10 to about 45 nodes depending upon branch length. The internode length is approximately 1 to 2 centimeters long. The shoot color is medium green (20-L-4) after white (20-A-1) waxy surface is wiped from new shoots.

The lenticel dimension is typically 5 mm, but ranging from 0.5 to 2 cm on trunks of 10 year old trees. The lenticel numbers are typically 18 lenticels/square inch (4–5 lenticels/square cm) on five-year-old wood. The lenticel color is orange-brown (12-J-10).

The bud position is both terminal and lateral. Lateral buds were conical in shape, pointed, and had dark brown scales (8-L-9). Multiple buds may be present at older nodes. The bud scales are generally dark brown (8-L-9), and nondistinctive.

Spurs are generally numerous, short and medium to stubby in width. Buds per spur are typically 0 to 3 lateral buds per spur. These will eventually become flower buds. On spurs which are one year old, the epidermis takes on a green (20-L-4) color, sometimes with red-brown (9-J-6) staining on the undersides of older gray-brown (8-E-7) spurs. The shape of terminal buds is pointed, small and dark brown. In contrast, lateral buds appear more rounded and have a lighter brown color (8-L-9). This color is not distinctive, however. Two year old wood generally appears darker in color from brown-green (20-K-4) to reddish brown (8-J-4) often with a white-gray (6-A-1) over-color. Three year old wood generally have many spurs and have persistent peduncles from which fruit has been borne on previous years. Stem scars are prominent. The color of three year old wood is white-gray (6-A-1) with some red-brown (8-J-4) undercolor. Four year old wood generally have a dull grayish brown (15-A-2) to light maroon (7-L-7) color. This color is not particularly distinctive, however. Some spurs continue to produce, but many spurs are clusters of persistent peduncles from earlier production.

Leaves: The quantity of leaves is abundant. There are typically 8 leaves for current season spur. The shape is considered lanceolate, occasionally elliptical, and tapering to the apex about ½ of the way from the apex. The tip shape is acuminate, and tapering to a more or less acute angle. The base angle is rounded to oblique. The size is generally smaller than 'Nonpareil'—approximately 30 to 90 millimeters. The width is approximately 10 to about 30 millimeters. The ratio of petiole length to leaf length is approximately 0.28. The ratio of blade width to blade length is approximately 0.30.

The color of the top surface is olive green (24-L-5). The color of the lower surface is yellow-green (22-J-6). The margin is crenate with rather shallow crenations. The venation is pinnately net veined. The leaf vein color is pale yellow (17-F-1).

The glands are usually 2 to 3, alternate on petiole, primarily at the base of leaf. The size is small. The form is globose. The color is yellow-orange (12-L-6). The typical size of small leaf glands are 0.5 mm.

The leaf petiole is medium length and thickness. The typical petiole length is 1.6 cm. The typical petiole diameter is 1.3 mm at base of fully expanded leaf. The petiole lower surface color is light yellow-green (17-J-3).

Bloom: Blooming period typically starts 2–4 days after 'Nonpareil', with full bloom occurring when 'Nonpareil' is at approximately 90% bloom.

The duration is approximately 14 days depending on season (similar to the Nonpareil variety) The amount of bloom is heavy. The color is white (3-A-1) with light pink (3-A-2) developing at the petal claw and then diffusing to petal sides with flower age.

The shape of petal apex is retuse, often with 1 to 3 shallow clefts on a rounded apex. The shape of petal base is base forms a narrowly cuneate, tapering claw. The configuration of petal margin is rounded, smooth to slightly crenate. The petal texture is soft, velvety, with slight puckering at margins. The majority of flowers contain five petals. Typically less than 3 percent of the flowers may contain 4, 6 or more petals.

Pollen: The pollen is partially self-compatible so that self-pollinations will result in greater than 10% set but not consistently greater tan 30% set. It is fully cross-compatible with 'Nonpareil' and 'Carmel' and so is capable of acting as a pollinizer for these and most commercial cultivars.

Crop: The crop harvest period is early season 1 to 2 weeks after 'Nonpareil'. It is a regular bearer. The nuts are well distributed on the tree. The nuts hang well on the tree and are easy to harvest and hull.

The productivity of the crop is heavy. Productivity is measured in the weight of the harvested kernels which have been removed from dried fruits. Average yields in Sacramento Valley test plots were 1,866 pounds per acre for 12-year-old trees as compared to 1,935 for 'Nonpareil' trees.

Fruit: Dried fruit and nuts can be stored for over a year. A high oleic acid content in the kernel oil confers high resistance to the development of oil rancidity in storage. Fruit and nuts show very low worm damage (<2%) when compared to damage on 'Nonpareil' (>30%) when stored in open bins.

*Immature fruit.*—The length at suture line is 32 mm. The width is 29 mm. The side view is uniformly elongate to ellipsoid. The dorsal edge is somewhat straight but sharply curving at the apical end and less so at the basal ends. The ventral edge is uniformly curving along entire length with oblique angle at basal end. The basal end angles at about 90° across and is rounded at dorsal side with oblique angles at ventral edge. The apical end is rounded with a very short acute protruding tip (stylar scar). The dorsal view shows both sides are uniform, slightly but uniformly curving. The ridge is largely inconspicuous and slightly uneven. The ventral view is similar to dorsal. Ventral suture line is slightly depressed. The apical end view is rounded with slightly conspicuous ridges. The basal view is rounded, noticeable suture line. The base scar is round to oval, and is medium in size. There is a clean separation. The hull dehiscence is along the ventral edge. The pubescence is whitish, very fine, and uniform. The surface is medium green (21-K-2) to yellow-green (21-K-5).

*Mature hull.*—The outer surface is smooth, pubescent. The form is uniform, symmetrical. The longitudinal section form is orbicular to cordate. The thickness, generally, is 1 to 3 mm when dry. The flesh is tough but brittle when dry. The suture is medium. The color is light green (21-J-1) occasionally with a reddish (6-J-3) blush. The dehiscence opens freely. There is splitting along suture. The nut cavity is ordate. The adherence can be described as hulls are easily removed from nuts by mechanical hullers.

*Mature in-shell nut.*—Typical length of the nut is length 2.74 cm and width is 2.22 cm. Typical thickness of the nut is 1.45 cm. Typical length of the fruit stem is 5 mm. Typical diameter of the fruit stem is 3 mm. The color of the fruit stem is lime-green (19-K-7). The size is medium to large. The form is cordate. The length/width is medium. The width/thickness is medium. The shell is a paper-type (i.e. easily cracked).

*Kernels.*—A kernel's average length is 21 mm. The average width is 13.5 mm. The average thickness is 8.1 mm. The average weight is 1.05 gram. The form is cordate or heart-shaped. The width/thickness is ovate. The base is ventrally oblique. The stem scar is large and obtuse. The apex is acuminate. The texture is furrowed. The pellicle is medium. The pubescence is smooth, veined. The color is light brown (12-J-6) with red-brown veins (13-H-12). The number of doubles is very low, less than 1%. The flavor is sweet.

The oil content average is 45.0% as compared to 43.5% for 'Nonpareil' variety. The oil quality is very high (74.9% Oleic acid content as compared to 67.5% for 'Nonpareil'). Higher oleic acid levels confer improved flavor, improved resistance to oil rancidity, and improved phytonutrient benefit to consumer). The quality is premium. It is blanchable.

Cultural characteristics: There is improved insect resistance to Navel orangeworm and Indian mealmoth as compared to 'Nonpareil'. The susceptibility to budfailure is low. The susceptibility to diseases is improved resistance to hull rot and noninfectious bud-failure as compared to 'Nonpareil'.

What is claimed is:

1. A new and distinct variety of almond tree substantially as shown and described herein.

* * * * *